United States Patent [19]

Markin

[11] Patent Number: 5,614,415
[45] Date of Patent: Mar. 25, 1997

[54] METHOD FOR AUTOMATIC TESTING OF LABORATORY SPECIMENS

[75] Inventor: Rodney S. Markin, Omaha, Nebr.

[73] Assignee: Board of Regents Univ of NE Lincoln, Lincoln, Nebr.

[21] Appl. No.: 435,859

[22] Filed: May 5, 1995

Related U.S. Application Data

[63] Continuation-in-part of Ser. No. 997,281, Dec. 23, 1992.

[51] Int. Cl.$^6$ .......................... G01N 35/04; G01N 35/02
[52] U.S. Cl. ................. 436/48; 422/69; 422/67; 436/47
[58] Field of Search ................. 436/47, 48; 422/63–65, 422/67

[56] References Cited

U.S. PATENT DOCUMENTS

| | | | |
|---|---|---|---|
| 3,533,744 | 10/1970 | Unger | 23/230 |
| 3,612,321 | 10/1971 | Larson | 215/7 |
| 3,660,638 | 5/1972 | Oberli | 235/61.6 R |
| 3,751,985 | 8/1973 | Knedel et al. | 73/423 A |
| 3,831,006 | 8/1974 | Chaffin, III et al. | 235/61.7 R |
| 3,898,433 | 8/1975 | Sallet | 235/61.11 R |
| 3,909,203 | 9/1975 | Young et al. | 23/253 R |
| 3,916,157 | 10/1975 | Roulette et al. | 235/61.12 R |
| 4,058,367 | 11/1977 | Gilford | 23/253 R |
| 4,857,471 | 8/1989 | Salzman et al. | 436/43 |
| 5,100,622 | 3/1992 | Mimura et al. | 422/67 |
| 5,350,564 | 9/1994 | Mazza et al. | 422/63 |
| 5,396,896 | 11/1994 | Margrey et al. | 436/48 |

FOREIGN PATENT DOCUMENTS

| | | |
|---|---|---|
| 3271164 | 11/1988 | Japan . |
| 1301167 | 12/1989 | Japan . |
| 4204159 | 7/1992 | Japan . |

Primary Examiner—Jill Warden
Assistant Examiner—Jan M. Ludlow
Attorney, Agent, or Firm—Zarley, McKee, Thomte Voorhees & Sease; Mark D. Frederiksen

[57] ABSTRACT

The method for automatic testing of a laboratory specimen of the present invention includes the initial step of obtaining a specimen to be tested and placing the specimen in a specimen container. Information regarding the specimen and any tests to be conducted thereon is entered into a computerized laboratory information system (LIS) which is connected to and communicates with a laboratory automation system (LAS) software. The specimen container is inserted in a specimen carrier, and the carrier marked with an identification code which uniquely identifies the specimen and, by virtue of the identification code, the tests to be conducted thereon. The specimen contained within the specimen carrier is entered into the LAS at a receiving station, which reads the identification code and thereby determines:

1. If tests which require process/steps which can run at variety of workstations;
2. If tests can have certain steps merged in an effort to ensure that they are carried out properly;
3. The priority of the specimen relative to other specimens already in the LAS;
4. The priority of each test to be conducted on the specimen; and
5. The most direct route from their receiving station to the workstation for conducting the highest priority test on the specimen.

5 Claims, 1 Drawing Sheet

METHOD FOR AUTOMATIC TESTING OF LABORATORY SPECIMENS

CROSS-REFERENCE TO RELATED APPLICATION

This is a continuation-in-part of Ser. No. 07/997,281 filed Dec. 23, 1992.

TECHNICAL FIELD

The present invention relates generally to laboratory automation systems, and more particularly to an improved method for automating a laboratory for the testing of individual laboratory specimens.

BACKGROUND OF THE INVENTION

Clinical laboratory testing has changed and improved remarkably over the past 70 years. Initially, tests or assays were performed manually, and generally utilized large quantities of serum, blood or other materials/body fluids. As mechanical technology developed in the industrial work place, similar technology was introduced into the clinical laboratory. With the introduction of new technology, methodologies were also improved in an effort to improve the quality of the results produced by the individual instruments, and to minimize the amount of specimen required to perform each test.

More recently, instruments have been developed to increase the efficiency of testing procedures by reducing turn around time and decreasing the volumes necessary to perform various assays. Present directions in laboratory testing focus on cost containment procedures and instrumentation. Laboratory automation is one area in which cost containment procedures are currently being explored. Robotic engineering has evolved to such a degree that various types of robots have been applied in the clinical laboratory setting.

The main focus of prior art laboratory automation relies on the implementation of conveyor systems to connect areas of the clinical laboratory. Known conveyor systems in the laboratory setting utilize separate conveyor segments to move specimens from a processing station to a specific laboratory workstation. In order to obtain cost savings, the specimens are sorted manually, and grouped in a carrier rack to be conveyed to a specific location. In this way, a carrier will move a group of 5–20 specimens from the processing location to the specific workstation to perform a single test, or a battery of tests, on each of the specimens in the carrier.

While grouping a plurality of specimens in a single carrier may be more cost efficient where every specimen requires only a single specific test, and none of the specimens within a carrier require special priority, it is not uncommon in the hospital environment for a specimen to be subjected to a variety of different tests, or for a particular specimen to require a very shod turn-around time (star testing). In such an event, the prior art automation systems could not be utilized, and the particular specimen would have to be manually moved to various work test stations based upon the time constraints and tests designated for the specimen.

Another problem with prior attempts at laboratory automation is in tracking the specimen and reporting the results of the specimen tested. Test results can serve as the basis for requiring additional testing of a particular specimen reflex or spawned testing. If the test results are required within a shod time period, rapid and efficient reporting of test results can improve laboratory quality and efficiency.

SUMMARY OF THE INVENTION

It is a general object of the present invention to provide a method for automating a clinical laboratory which permits individual and independent assignment of a specimen to one or more of a plurality of workstations within the laboratory.

Another object of the present invention is to provide a method for automating a clinical laboratory which can prioritize individual specimens to improve turn around time for the testing of an individual specimen.

A further object is to provide a method for automating a laboratory which determines optional routing to a particular workstation, and detects any time delays because of other specimens present in a queue at a workstation.

An additional object is to provide a method of automating a laboratory wherein the tracking and transportation are independent of the mechanism; i.e., automated guided vehicles and conveyor systems may be used interchangeably.

Still another object of the present invention is to provide a method for automating a clinical laboratory which tracks a specimen location throughout the laboratory and reports test results to a central database for immediate review by a physician.

These and other objects will be apparent to those skilled in the art.

The method for automatic testing of a laboratory specimen of the present invention includes the initial step of obtaining a specimen to be tested and placing the specimen in a specimen container. Information regarding the specimen and any tests to be conducted thereon is entered into a computerized laboratory information system (LIS) which is connected to and communicates with a laboratory automation system (LAS) software. The specimen container is inserted in a specimen carrier, and the carrier marked with an identification code which uniquely identifies the specimen and, by virtue of the identification code, the tests to be conducted thereon. The specimen contained within the specimen carrier is entered into the LAS at a receiving station, which reads the identification code and thereby determines:

1. If tests which require process/steps which can run at variety of workstations;
2. If tests can have certain steps merged in an effort to ensure that they are carried out properly;
3. The priority of the specimen relative to other specimens already in the LAS;
4. The priority of each test to be conducted on the specimen; and
5. The most direct route from their receiving station to the workstation for conducting the highest priority test on the specimen.

The carrier is then entered into the LAS by directing the carrier onto a conveyor or other transport media connecting all of the workstations of the laboratory. The LAS software will operate a gate at the appropriate workstation to direct the carrier to an auxiliary conveyor at the workstation. Upon directing the carrier to the appropriate workstation, the LAS software recalculates the priority of all specimens in the LAS. After completion of a test, a carrier is returned to the conveyor or other transport media of the LAS and directed to any subsequent workstations for other testing, or to an archiving station for temporary or permanent storage or disposal of the specimen.

DESCRIPTION OF THE PREFERRED EMBODIMENT

Figure 1:
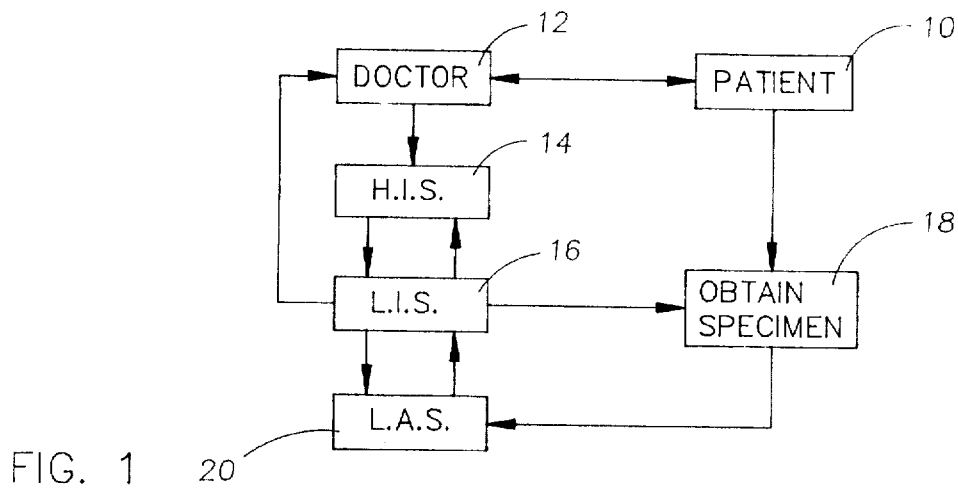
FIG. 1 is a flow chart showing the integration of a laboratory automation system with a laboratory information system and hospital information system.

Referring now to the drawings, FIG. 1 is a flowchart showing how the laboratory automation system (LAS) of the present invention integrates with the day-to-day operations of a hospital. Box 10 refers to any patient who is in need of examination and/or diagnosis. Box 12 represents the relevant physician or other practitioner who will interpret the results of the examination in order to determine the necessity of tests and the priority level to be given various required tests, in order to make a final diagnosis and/or prescribe a specified treatment. Information passes in both directions between doctor and patient during this examination.

As a result of the examination, the doctor will make a record of the examination results, and may enter a request for a specific test(s) to be performed and designate the priority level of the test(s). This information is entered in the general hospital information system (HIS) shown as box 14 in the flowchart. The HIS will correlate patient identification information, room information, as well as any insurance or other typical general information necessary for operation of a hospital. The HIS is a computer system which communicates with various areas of the hospital to integrate all functions of the hospital.

Once the doctor's test order is correlated with the patient identification information, the HIS will forward the correlated information to the laboratory information system (LIS) designated as box 16 in the FIG. 1. The LIS is a computer system which may be connected to the HIS to quickly and efficiently communicate information.

As shown in FIG. 1, the LIS assigns the task of obtaining a specimen to an appropriate technician, the retrieval of the specimen being designated generally at box 18. The physical specimen(s) obtained from the patient is then entered in the laboratory automation system (LAS) designated generally as box 20. The LAS takes the place of prior art manual testing procedures, including the reporting of the test results to the LIS. The LIS communicates with the LAS to order specific tests related to a specific specimen, and receive the results of those tests. The LIS may also communicate with the HIS to report test results for accounting and insurance purposes. The LIS reports either to the doctor via a separate workstation, or via the HIS, to report the results of the requested tests.

Figure 2:
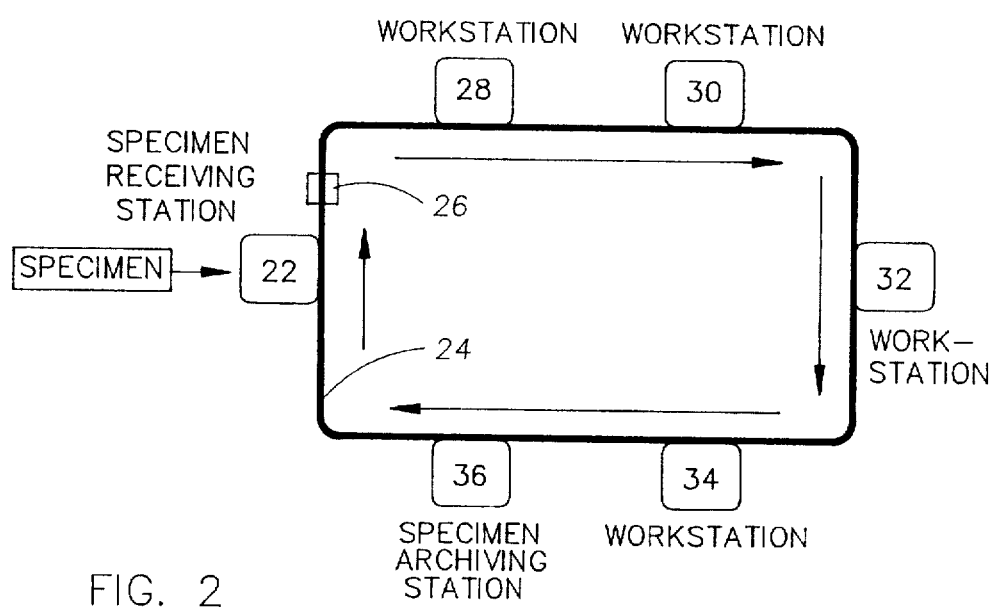
FIG. 2 is a schematic diagram of specimen movement through a laboratory automation system.

Referring now to FIG. 2, a schematic diagram of specimen movement throughout the laboratory automation system is shown. The specimen arrives at a specimen receiving station 22, where the specimen is entered on a conveyor system designated generally at 24. During the assignment of the task of obtaining a specimen, the laboratory information system would also provide a specimen container marked with an appropriate patient identification code. The inventor has found that a conventional bar code label applied to the specimen container is a simple and efficient method for fulfilling this function. Since most specimen containers are not designed for transport on a conveyor system, a separate carrier 26 is provided to support an individual specimen container on conveyor system 24. At specimen receiving station 22, the carrier 26 is given an identification code which correlates with the specimen container and the specimen to be tested, so that the container and carrier may be directed throughout the laboratory automation system, even when the specimen container is removed from the carrier for specific testing at a workstation.

As shown in FIG. 2, conveyor system 24 is preferably a continuously moving conveyor which will move carriers 26 in a generally closed loop system. At receiving station 22, the carrier assignment is entered into the LAS to determine which workstations the specimen must utilize, the order in which the stations are to be utilized, the priority of the particular tests to be conducted or steps to be taken, and any other pertinent information with respect to priority or turnaround time. Entry of this information may be as simple as scanning the bar code of the carrier with a bar code reader.

While FIG. 2 shows only 4 specific workstations, 28, 30, 32, and 34, obviously a conventional clinical laboratory could have a wide variety of such stations throughout a facility. The closed loop system of conveyor 24 permits a specimen to stop at any given workstation in any particular order. Thus, if time constraints require that the test of workstation 34 be performed first, and that a test of workstation 32 be performed at some time after the test of workstation 34, the specimen can travel on conveyor 24 past workstations 30 and 32, directly to workstation 34, for immediate testing. Carrier 26 is then reintroduced on conveyor system 24 to follow the closed loop around to the next workstation assigned to the specimen. Once the testing has been completed, the specimens are forwarded to the specimen archiving station 36 for removal from conveyor 24 and appropriate storage.

Figure 3:
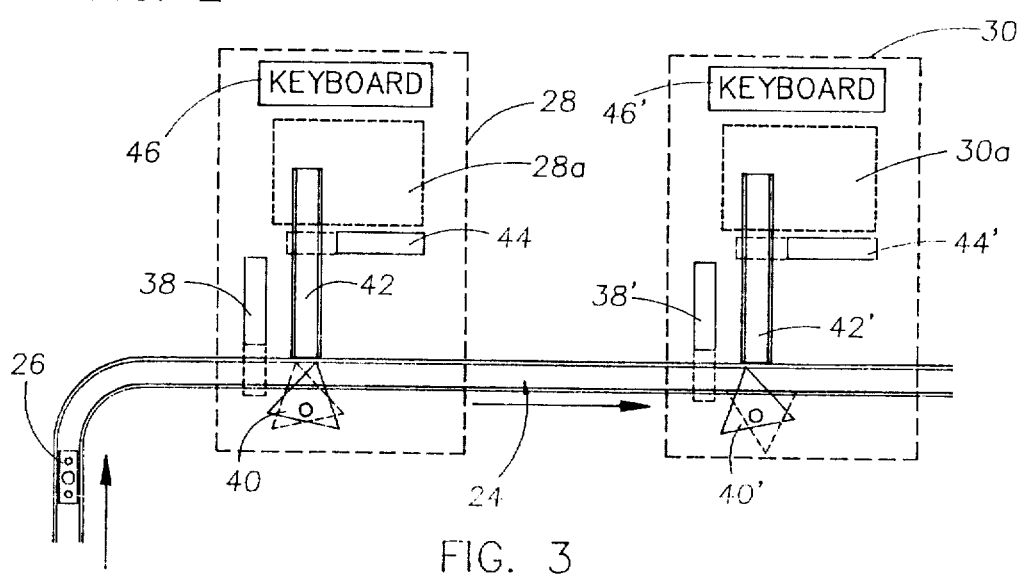
FIG. 3 is an enlarged schematic view of the specimen processing station and one workstation along the schematic of FIG. 2.

Referring now to FIG. 3, an enlarged view of a portion of the schematic of FIG. 2 is shown. Workstations 28 and 30 are shown in schematic view to demonstrate portions of the method for detecting and routing specimens at each specific workstation located along conveyor system 24. As carrier 26 moves along conveyor 24, it will pass within the zone of workstation 28 where a sensor 38 will detect the identification code on carrier 26. In the preferred embodiment of the invention, sensor 38 is a bar code reader while the identification code on the carrier 26 is a bar code. Sensor 38 is connected with the LAS, to record the movement of carrier 26, and determine routing of the carrier.

A gate 40 is connected to the LAS and will be activated to redirect the movement of carrier 26 off of conveyor 24 and on to an auxiliary conveyor 42 to reach the testing area 28a within the workstation 28. Testing area 28a may be comprised of manual testing, fully automatic mechanical testing, or partially automated testing. An additional sensor 44 is positioned along auxiliary conveyor 42 to track the location of the carrier and specimen, and may be utilized to activate any automatic mechanical equipment associated with the testing area 28a.

As discussed above, the computer system of the LAS will direct the movement of the specimen to the appropriate workstation at the appropriate time. A keyboard 46, or the like, is provided at each workstation to enter test results into the LIS, which in turn distributes the appropriate instructions to the pertinent sensors and workstations, as described in more detail hereinbelow. Once testing has been completed, the specimen is again loaded in specimen carrier 26 and placed in conveyor system 24 by auxiliary conveyor 42.

If the particular test requested by the physician is performed at workstation 30, then the receiving station 22 will determine the optimal route to workstation 30, while simultaneously determining the priority of the requested test for carrier 26 relative to other specimen carriers in the system along conveyor 24. Sensors 38 at each gate 40 of each workstation serve to detect the relative location of the carrier as well as the states of the gate 40 of the workstation. Each sensor 44 detects the presence of a carrier at the testing zone of the particular workstation, as well as the number of other carriers which are queued in line for testing at the particular workstation.

In this example, sensor 38' will acknowledge the passage of carrier 26 thereby, thereby triggering the LIS to direct gate 40' to divert the carrier 26 onto the auxiliary conveyor 42' of workstation 30. A sensor 34' will then direct the specimen to the appropriate testing area 30a.

Once the carrier has been directed into the queue of workstation 30, the priority table of all carriers in the LAS is recalculated to again direct the next highest priority specimen along the optimal route to the requested workstation.

Once the test performed by workstation 30 has been completed, the results are transmitted from the work area 30a to the LIS by virtue of keyboard 46', and the specimen is loaded in the specimen carrier 26 and positioned on auxiliary conveyor 42'. The priority of any subsequent testing is then recalculated in the LAS priority table. The specimen will then be moved to the main conveyor system 24 for movement to the next appropriate station.

Workstations 32 and 34 are not shown in detail, but include the same basic equipment as workstations 28 and 30. Thus, a sensor 38' located at workstations 32 and 34 will acknowledge passage of the specimen at that location and either direct the specimen into the workstation, or direct the specimen to continue past the workstation. If the order in which the tests are conducted is important, the specimen can be directed to bypass any workstation along the conveyor system 24 so as to immediately reach the highest priority workstation to perform the appropriate testing. Since the conveyor system is a closed loop, the specimen can then be moved around the loop to any other workstation.

Once all requested tests have been performed, the specimen will be directed into the specimen archiving station utilizing a sensor 38' and gate 40' in the same manner as workstations 28, 30, 32 and 34. Since every sensor 38, 38', 44 and 44' is interconnected by way of the LAS, the location and status of any specimen is always readily accessible by the doctor. Since the LIS is programmable, the doctor can call for additional tests at any time during the movement of the specimen within the LAS. This ability to direct an individual specimen to one or more of a plurality of workstations decreases the turn-around time and increases the versatility of the automation system. With the use of robotics, and a fully integrated laboratory instrumentation, it is possible to fully automate the entire laboratory automation system.

The results of standard testing may conventionally require additional testing. In such a case, the LIS may automatically assign additional or different workstation stops based upon the results received from a test at any given workstation. The capability of prioritizing the testing also permits a doctor to diagnose and/or otherwise individualize the test battery which is required for an individual patient.

Whereas the invention has been shown and described in connection with the preferred embodiment thereof, it will be understood that many modifications, substitutions and additions may be made which are within the intended broad scope of the appended claims. There has therefore been shown and described an improved method for automatic testing of laboratory specimen.

I claim:

1. A method for routing a specimen through an automated laboratory system, comprising the steps of:

placing a first specimen to be tested in a specimen container;

inputting information regarding the specimen and tests to be conducted on the specimen into a computerized laboratory information system (LIS) which is connected to and communicates with a laboratory automation system (LAS);

marking a first carrier with an identification code identifying the first specimen and tests to be conducted thereon;

placing the first specimen in the first carrier and entering the first carrier into the LAS at a receiving station;

at the receiving station, the LAS reading the identification code and calculating:

the priority of the first specimen relative to any other specimens entered into the LAS;

the priority of each test to be conducted on the first specimen relative to one another; and the most direct route from the receiving station to a first workstation for conducting the highest priority test of the first specimen;

entering the first carrier into the LAS by directing the carrier onto a conveyor of the LAS, the conveyor extending among a plurality of workstations, each workstation adapted to conduct a predetermined test;

the LAS operating the conveyor system to direct the first carrier to the first workstation;

the LAS operating a gate at the first workstation to direct the carrier to a workstation auxiliary conveyor, for conducting a test on the specimen; and the LAS recalculating the priority of the first specimen and any other specimens in the LAS upon directing of the first carrier to the first workstation.

2. The method of claim 1, further comprising the steps of:

conducting the first predetermined test on the first specimen after the step of directing the first carrier to the first workstation auxiliary conveyor;

directing the first carrier back to the conveyor system of the LAS upon completion of the test; and the LAS reading the identification code and determining a subsequent location for the first carrier upon reentry of the carrier onto the LAS conveyor system, based upon the information originally inputted into the LAS.

3. The method of claim 2, further comprising the step of the LAS directing the carrier along the conveyor system to an archiving station for storage of the first specimen, upon completion of all tests, the LAS removing the first specimen from calculations of priorities upon the directing of the specimen to the archiving station.

4. The method of claim 1, further comprising the steps of:

providing a sensor at each gate along the conveyor system for reading the identification code on a carrier on the conveyor system, the LIS being connected to each sensor for communication therewith;

the LAS tracking a presence of a carrier at each sensor and identifying the carrier and location thereof.

5. The method of claim 1, further comprising the steps of:

inputting the results of tests conducted on said first specimen into the LAS;

the LAS updating its database with the first specimen tests results, and recalculating the priority of any additional tests to be conducted on the first specimen, in response to the updating of the database.

\* \* \* \* \*

UNITED STATES PATENT AND TRADEMARK OFFICE
CERTIFICATE OF CORRECTION

PATENT NO.   : 5,614,415
DATED        : March 25, 1997
INVENTOR(S)  : Rodney S. Markin It is certified that error appears in the above-indentified patent and that said Letters Patent is hereby corrected as shown below:

In claim 4, line 4, change "LIS" to --LAS--.

Signed and Sealed this

Twenty-sixth Day of August, 1997

Attest:

BRUCE LEHMAN

Attesting Officer

Commissioner of Patents and Trademarks